United States Patent [19]
Stevenson

[11] Patent Number: 5,723,411
[45] Date of Patent: Mar. 3, 1998

[54] HERBICIDAL PYRIDAZINONES

[75] Inventor: Thomas Martin Stevenson, Newark, Del.

[73] Assignee: E. I. du Pont de Nemours and Company, Wilmington, Del.

[21] Appl. No.: 732,001

[22] Filed: Oct. 16, 1996

Related U.S. Application Data

[60] Provisional application No. 60/006,094 Oct. 31, 1995.

[51] Int. Cl.$^6$ .............. A01N 43/58; C07D 405/10; C07D 417/10; C07D 237/16
[52] U.S. Cl. .............. 504/238; 504/229; 504/230; 544/114; 544/182; 544/215; 544/230; 544/238; 544/239; 544/240; 544/241
[58] Field of Search .............. 544/238, 239, 544/240, 241, 230, 114; 504/238

[56] References Cited

FOREIGN PATENT DOCUMENTS

| 0 249 149 | 12/1987 | European Pat. Off. . |
|---|---|---|
| WO 88/04652A1 | 6/1988 | WIPO . |

OTHER PUBLICATIONS

Chantegrel et al, *J. Het. Chem.* 27 pp. 927–934 (1990).

*Primary Examiner*—Emily Bernhardt

[57] ABSTRACT

Compounds of Formula I, and their N-oxides and agriculturally-suitable salts, are disclosed which are useful for controlling undesired vegetation

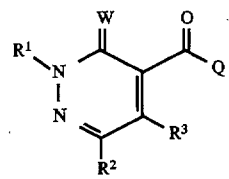

wherein Q, W, R$^1$, R$^2$ and R$^3$ are as defined in the disclosure.

Also disclosed are compositions containing the compounds of Formula I and a method for controlling undesired vegetation which involves contacting the vegetation or its environment with an effective mount of a compound of Formula I.

4 Claims, No Drawings

HERBICIDAL PYRIDAZINONES

CROSS-REFERENCE TO RELATED APPLICATION

This application is a continuation-in-part of U.S. Provisional Application No. 60/006,094, filed Oct. 31, 1995.

BACKGROUND OF THE INVENTION

This invention relates to certain pyridazinones, their N-oxides, agriculturally-suitable salts and compositions, and methods of their use for controlling undesirable vegetation.

The control of undesired vegetation is extremely important in achieving high crop efficiency. Achievement of selective control of the growth of weeds especially in such useful crops as rice, soybean, sugar beet, corn (maize), potato, wheat, barley, tomato and plantation crops, among others, is very desirable. Unchecked weed growth in such useful crops can cause significant reduction in productivity and thereby result in increased costs to the consumers. The control of undesired vegetation in noncrop areas is also important. Many products are commercially available for these purposes, but the need continues for new compounds which are more effective, less costly and environmentally safe.

SUMMARY OF THE INVENTION

This invention is directed to compounds of Formula I including all geometric and stereoisomers, N-oxides, and agriculturally suitable salts thereof, agricultural compositions containing them and their use for controlling undesirable vegetation:

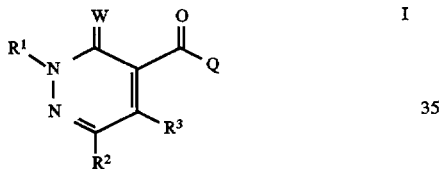

wherein

Q is phenyl, 1H-pyrrolyl, furanyl, thienyl, 1H-pyrazolyl, 1H-imidazolyl, isoxazolyl, oxazolyl, isothiazolyl, thiazolyl, 1H-1,2,3-triazolyl, 2H-1,2,3-triazolyl, 1H-1,2,4-triazolyl, 4H-1,2,4-triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1H-tetrazolyl, 2H-tetrazolyl, pyridinyl, pyridazinyl, pyrimidinyl, pyrazinyl, 1,3,5-triazinyl, 1,2,4-triazinyl, or 1,2,4,5-tetrazinyl, each ring substituted with $R^4$ and optionally substituted with up to three $R^5$; or Q is an 8 to 10-membered fused bicyclic aromatic ring system, each bicyclic ring system containing 0 to 4 heteroatoms independently selected from the group nitrogen, oxygen, and sulfur, provided that the bicyclic ring system contains no more than 4 nitrogens, no more than 2 oxygens, and no more than 2 sulfurs, each ring system substituted with one to four $R^5$;

W is O or S;

$R^1$ is H, $C_1$–$C_6$ alkyl, $C_1$–$C_6$ haloalkyl, $C_3$–$C_6$ alkenyl, $C_3$–$C_6$ haloalkenyl, $C_3$–$C_6$ alkynyl, $C_3$–$C_6$ haloalkynyl, or $C_3$–$C_6$ cycloalkyl;

$R^2$ is H, $C_1$–$C_3$ alkyl, $C_1$–$C_3$ haloalkyl, $C_1$–$C_3$ alkoxy, halogen, or cyano;

$R^3$ is $OR^6$, $C_1$–$C_6$ alkylthio, $C_1$–$C_6$ haloalkylthio, $C_1$–$C_6$ alkylsulfinyl, $C_1$–$C_6$ haloalkylsulfinyl, $C_1$–$C_6$ alkylsulfonyl, $C_1$–$C_6$ haloalkylsulfonyl, mercapto, or halogen;

$R^4$ is $C_1$–$C_4$ alkyl, $C_1$–$C_4$ haloalkyl, $OR^7$, $S(O)_mR^8$, $S(O)_2NR^9R^{10}$, $C(=O)R^8$, $C(=O)OR^8$, $C(=O)NR^9R^{10}$, $NR^{11}R^{12}$, halogen, cyano, or nitro;

each $R^5$ is independently $C_1$–$C_4$ alkyl, $C_1$–$C_4$ haloalkyl, $OR^7$, $S(O)_mR^8$, $S(O)_2NR^9R^{10}$, $C(=O)R^8$, $C(=O)OR^8$, $C(=O)NR^9R^{10}$, $NR^{11}R^{12}$, halogen, cyano, or nitro; or when $R^4$ and an $R^5$ are attached to adjacent atoms on Q, $R^4$ and said adjacently attached $R^5$ can be taken together as $C_3$–$C_5$ alkylene, $C_3$–$C_5$ alkenylene, —$(CH_2)_n$—X—, —$(CH_2)_p$—X—$CH_2$—, —$CH_2CH_2$—X—$CH_2CH_2$—, —$CH_2CH=CH$—X—, —$CH=CHCH_2$—X—, —$CH=CH$—X—$CH_2$—, —X—$CH_2$—X—, —X—$CH_2CH_2$—X—, —$CH_2$—X—$CH_2$—X—, —X—$CH=CH$—X—, —$(CH_2)_p$—$NR^{13}$—$S(O)_2$—, or —$(CH_2)_p$—$S(O)_2$—$NR^{13}$—, each group optionally substituted with one to five $R^{14}$;

each X is independently O, $S(O)_m$, or $NR^{13}$;

$R^6$ is H, $C_1$–$C_6$ alkyl, $C_1$–$C_6$ haloalkyl, $C_2$–$C_6$ alkoxyalkyl, formyl, $C_2$–$C_6$ alkylcarbonyl, $C_2$–$C_6$ alkoxycarbonyl, $C_2$–$C_6$ alkylaminocarbonyl, $C_3$–$C_7$ dialkylaminocarbonyl, $C_1$–$C_6$ alkylsulfonyl, or $C_1$–$C_6$ haloalkylsulfonyl; or $R^6$ is benzoyl or phenylsulfonyl, each optionally substituted with $C_1$–$C_3$ alkyl, halogen, cyano, or nitro;

each $R^7$ is independently $C_1$–$C_4$ alkyl, $C_1$–$C_4$ haloalkyl, $C_3$–$C_5$ cycloalkyl, $C_4$–$C_6$ cycloalkylalkyl, $C_2$–$C_6$ alkoxyalkyl, $C_2$–$C_5$ cyanoalkyl, formyl, $C_2$–$C_5$ alkylcarbonyl, $C_2$–$C_5$ alkoxycarbonyl, $C_1$–$C_4$ alkylsulfonyl, or $C_1$–$C_4$ haloalkylsulfonyl;

each $R^8$ is independently $C_1$–$C_4$ alkyl, $C_1$–$C_4$ haloalkyl, $C_3$–$C_5$ cycloalkyl, $C_4$–$C_6$ cycloalkylalkyl, $C_2$–$C_6$ alkoxyalkyl, or $C_2$–$C_5$ cyanoalkyl; each $R^9$ is independently H, $C_1$–$C_6$ alkyl, $C_1$–$C_6$ haloalkyl, $C_3$–$C_6$ alkenyl, $C_3$–$C_6$ haloalkenyl, $C_3$–$C_6$ alkynyl, $C_3$–$C_6$ haloalkynyl, or $C_1$–$C_6$ alkoxy; or $R^9$ is phenyl or benzyl, each optionally substituted on the phenyl ring with $C_1$–$C_3$ alkyl, halogen, cyano, or nitro;

each $R^{10}$ is independently H, $C_1$–$C_6$ alkyl, $C_1$–$C_6$ haloalkyl, $C_3$–$C_6$ alkenyl, $C_3$–$C_6$ haloalkenyl, $C_3$–$C_6$ alkynyl, or $C_3$–$C_6$ haloalkynyl; or each pair of $R^9$ and $R^{10}$, when attached to the same atom, can independently be taken together as —$CH_2CH_2$—, —$CH_2CH_2CH_2$—, —$CH_2CH_2CH_2CH_2$—, —$CH_2CH_2CH_2CH_2CH_2$—, or —$CH_2CH_2OCH_2CH_2$—, each group optionally substituted with 1–2 $C_1$–$C_3$ alkyl;

each $R^{11}$ is independently H, $C_1$–$C_4$ alkyl, $C_1$–$C_4$ haloalkyl, $C_3$–$C_5$ cycloalkyl, $C_4$–$C_6$ cycloalkylalkyl, $C_2$–$C_6$ alkoxyalkyl, $C_2$–$C_5$ cyanoalkyl, formyl, $C_2$–$C_5$ alkylcarbonyl, $C_2$–$C_5$ alkoxycarbonyl, $C_1$–$C_4$ alkylsulfonyl, or $C_1$–$C_4$ haloalkylsulfonyl;

each $R^{12}$ is independently H, $C_1$–$C_6$ alkyl, $C_1$–$C_6$ haloalkyl, $C_3$–$C_6$ alkenyl, $C_3$–$C_6$ haloalkenyl, $C_3$–$C_6$ alkynyl, $C_3$–$C_6$ haloalkynyl, or $C_1$–$C_6$ alkoxy; or $R^{12}$ is phenyl or benzyl, each optionally substituted on the phenyl ring with $C_1$–$C_3$ alkyl, halogen, cyano, or nitro; or each pair of $R^{11}$ and $R^{12}$, when attached to the same atom, can independently be taken together as —$CH_2CH_2$—, —$CH_2CH_2CH_2$—, —$CH_2CH_2CH_2CH_2$—, —$CH_2CH_2CH_2CH_2CH_2$—, or —$CH_2CH_2OCH_2CH_2$—, each group optionally substituted with 1–2 $C_1$–$C_3$ alkyl;

$R^{13}$ is H or $C_1$–$C_4$ alkyl;

each $R^{14}$ is independently $C_1$–$C_6$ alkyl, $C_1$–$C_6$ haloalkyl, $C_1$–$C_6$ alkoxy, $C_1$–$C_6$ haloalkoxy, $C_1$–$C_6$ alkylthio, $C_1$–$C_6$ haloalkylthio, hydroxy, or halogen; or two $R^{14}$ bonded to the same carbon atom can be taken together as —$OCH_2CH_2O$—, —$OCH_2CH_2CH_2O$—, —$SCH_2CH_2S$—, or —$SCH_2CH_2CH_2S$—, each $CH_2$ optionally substituted with 1–2 $CH_3$ or 1–2 halogen; or two $R^{14}$ bonded to the same carbon atom can be taken together with the carbon to which they are attached to form C(=O), C(=S) or C(=N—$OR^{15}$); provided that when two $R^{14}$ groups are attached to a carbon atom which is attached to an X, then said $R^{14}$ groups are other than taken together as optionally substituted —$OCH_2CH_2O$—, —$OCH_2CH_2CH_2O$—, —$SCH_2CH_2S$—, or —$SCH_2CH_2CH_2S$— and no more than one of said $R^{14}$ groups can be $C_1$–$C_6$ alkoxy, $C_1$–$C_6$ haloalkoxy, $C_1$–$C_6$ alkylthio, $C_1$–$C_6$ haloalkylthio, or hydroxy;

each $R^{15}$ is independently H, $C_1$–$C_6$ alkyl, $C_1$–$C_6$ haloalkyl, $C_3$–$C_6$ alkenyl, or $C_3$–$C_6$ alkynyl;

each m is independently 0, 1, or 2; and each p is independently 1, 2, or 3.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. The term "1–2 alkyl" indicates that one or two of the available positions for that substituent may be alkyl. "Alkenyl" includes straight-chain or branched alkenes such as 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as 1-propynyl, 2-propynyl and the different butynyl, pentynyl and hexynyl isomers. "Alkynyl" can also include moieties comprised of multiple triple bonds such as 2,5-hexadiynyl. "Alkylene" denotes a straight-chain alkanediyl. Examples of "alkylene" include $CH_2CH_2CH_2$, $CH_2CH_2CH_2CH_2$ and $CH_2CH_2CH_2CH_2CH_2$. "Alkenylene" denotes a straight-chain alkenediyl containing one olefinic bond. Examples of "alkenylene" include CH=$CHCH_2$, $CH_2$CH=$CHCH_2$ and CH=$CHCH_2CH_2CH_2$. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3$S(O), $CH_3CH_2$S(O), $CH_3CH_2CH_2$S(O), $(CH_3)_2$CHS(O) and the different butylsulfinyl, pentylsulfinyl and hexylsulfinyl isomers. Examples of "alkylsulfonyl" include $CH_3$S(O)$_2$, $CH_3CH_2$S(O)$_2$, $CH_3CH_2CH_2$S(O)$_2$, $(CH_3)_2$CHS(O)$_2$ and the different butylsulfonyl, pentylsulfonyl and hexylsulfonyl isomers. "Cyanoalkyl" denotes an alkyl group substituted with one cyano group. Examples of "cyanoalkyl" include $NCCH_2$, $NCCH_2CH_2$ and $CH_3$CH(CN)$CH_2$. "Alkylamino", "dialkylamino", and the like, are defined analogously to the above examples. "Cycloalkyl" includes, for example, cyclopropyl, cyclobutyl, cyclopentyl, and cyclohexyl. Examples of "cycloalkylalkyl" include cyclopropylmethyl, cyclobutylethyl, and other cycloalkyl moieties bonded to straight-chain or branched alkyl groups. The term "aromatic ring system" denotes fully unsaturated carbocycles and heterocycles in which the polycyclic ring system is aromatic (where aromatic indicates that the Hackel rule is satisfied for the ring system). The aromatic ring systems can be attached through any available carbon or nitrogen by replacement of a hydrogen on said carbon or nitrogen.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "haloalkoxy", and the like, are defined analogously to the term "haloalkyl". Examples of "haloalkenyl" include $(Cl)_2$C=$CHCH_2$ and $CF_3CH_2$CH=$CHCH_2$. Examples of "haloalkynyl" include HC≡$CCHCl$, $CF_3$C≡C, $CCl_3$C≡C and $FCH_2$C≡$CCH_2$. Examples of "haloalkoxy" include $CF_3O$, $CCl_3CH_2O$, $HCF_2CH_2CH_2O$ and $CF_3CH_2O$. Examples of "haloalkylthio" include $CCl_3$S, $CF_3$S, $CCl_3CH_2$S and $ClCH_2CH_2CH_2O$. Examples of "haloalkylsulfonyl" include $CF_3$S(O)$_2$, $CCl_3$S(O)$_2$, $CF_3CH_2$S(O)$_2$ and $CF_3CF_2$S(O)$_2$.

The total number of carbon atoms in a substituent group is indicated by the "$C_i$–$C_j$" prefix where i and j are numbers from 1 to 7. For example, $C_1$–$C_3$ alkylsulfonyl designates methylsulfonyl through propylsulfonyl; $C_2$ alkoxyalkyl designates $CH_3OCH_2$; $C_3$ alkoxyalkyl designates, for example, $CH_3$CH(OCH$_3$), $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2O$ $CH_2$ and $CH_3CH_2O$ $CH_2CH_2$. Examples of "alkylcarbonyl" include C(O)$CH_3$, C(O)$CH_2CH_2CH_3$ and C(O)CH(CH$_3$)$_2$. Examples of "alkoxycarbonyl" include $CH_3$OC(=O), $CH_3CH_2$OC(=O), $CH_3CH_2CH_2$OC(=O), (CH$_3$)$_2$CHOC(=O) and the different butoxy- or pentoxycarbonyl isomers. In the above recitations, when a compound of Formula I is comprised of one or more heterocyclic rings, all substituents are attached to these rings through any available carbon or nitrogen by replacement of a hydrogen on said carbon or nitrogen.

When a compound is substituted with a substituent bearing a subscript that indicates the number of said substituents can exceed 1, said substituents (when they exceed 1) are independently selected from the group of defined substituents. Further, when the subscript indicates a range, e.g. (R)$_{i-j}$, then the number of substituents may be selected from the integers between i and j inclusive.

When a group contains a substituent which can be hydrogen, for example $R^1$ or $R^6$, then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula I, N-oxides and agriculturally suitable salts thereof. The compounds of the invention may be present as a mixture of stereoisomers, individual stereoisomers, or as an optically active form.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic group.

Preferred compounds for reasons of better activity and/or ease of synthesis are:

Preferred 1. Compounds of Formula I above, and N-oxides and agriculturally-suitable salts thereof, wherein:

Q is phenyl, 1H-pyrrolyl, furanyl, thienyl, 1H-pyrazolyl, 1H-imidazolyl, isoxazolyl, oxazolyl, isothiazolyl, thiazolyl, 1H-1,2,3-triazolyl, 2H-1,2,3-triazolyl, 1H-1,2,4-triazolyl, 4H-1,2,4-triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1H-tetrazolyl, 2H-tetrazolyl, pyridinyl, pyridazinyl, pyrimidinyl, pyrazinyl, 1,3,5-triazinyl, 1,2,4-triazinyl, or 1,2,4,5-tetrazinyl, each ring substituted with $R^4$ and optionally substituted with up to three $R^5$; or Q is naphthalenyl, azulenyl, indolizinyl, 1H-indolyl, benzofuranyl, benzo[b]thiophenyl, 1H-indazolyl, 1H-benzimidazolyl, 1,2-benzisoxazolyl, benzoxazolyl, 1,2-benzisothiazolyl, benzothiazolyl, quinolinyl, isoquinolinyl, cinnolinyl, phthalazinyl, quinazolinyl, quinoxalinyl, 1,8-naphthyridinyl, 7H-purinyl, pteridinyl, pyrazolo[5,1-b]thiazolyl, thiazolo[2,3-c]-1,2,4-triazolyl, [1,2,4]triazolo[1,5-a]pyridinyl, and thieno[3,2-d]thiazolyl, each ring system substituted with one to four $R^5$.

Preferred 2. Compounds of Preferred 1 wherein:

Q is phenyl substituted with $R^4$ and optionally substituted with up to three $R^5$ provided that, when $R^4$ and an adjacently attached $R^5$ are taken together, then Q is selected from the group

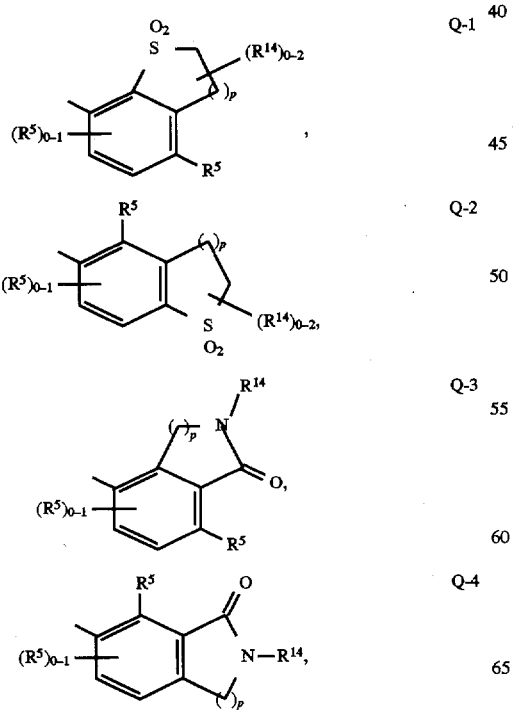

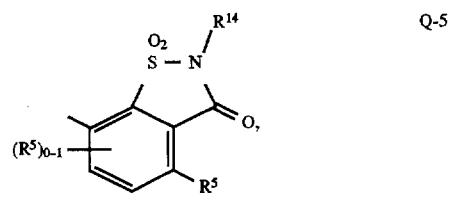

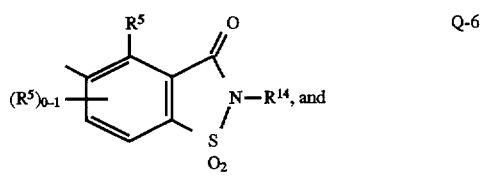

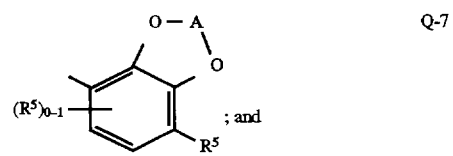

A is —$CH_2$— or —$CH_2CH_2$—, each group optionally substituted with 1–4 halogen.

Most preferred is the compound of Preferred 2 which is:

4-[(3,4-dihydro-4,4,5,8-tetramethyl-2H-1-benzothiopyran-6-yl) carbonyl]-5-hydroxy-2-methyl-3(2H)-pyridazinone S,S-dioxide.

This invention also relates to herbicidal compositions comprising herbicidally effective amounts of the compounds of Formula I and at least one of a surfactant, a solid diluent or a liquid diluent. The preferred compositions of the present invention are those which comprise the above preferred compounds.

This invention also relates to a method for controlling undesired vegetation comprising applying to the locus of the vegetation herbicidally effective amounts of the compounds of Formula I (e.g., as a composition described herein). The preferred methods of use are those involving the above preferred compounds.

DETAILS OF THE INVENTION

The compounds of Formula I can be prepared by the following methods and variations as described in Schemes 1–10. The definitions of Q, W, $R^1$, $R^2$ and $R^3$ in the compounds of Formulae I–X below are as defined above in the Summary of the Invention.

Compounds of Formula I ($R^3$=OH) can be obtained by the dealkylation of compounds of Formula II as shown in Scheme 1. Boron tribromide is preferred for the dealkylation. The alkoxy compound (II) is treated with boron tribromide in a chlorinated hydrocarbon solvent. The reaction is typically carried out at room temperature, but may be carried out at more elevated temperatures. Other conditions and reagents for dealkylation are described by Larock, *Comprehensive Organic Transformations*, VCH publishing, New York, (1989) pp 501 to 504.

Scheme 1

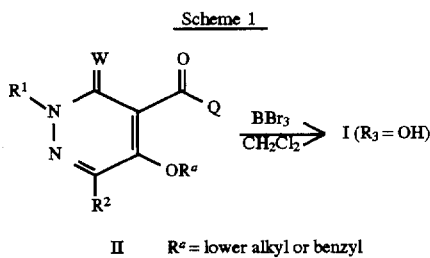

II    R$^a$ = lower alkyl or benzyl

The ketones of Formula II can be obtained by the oxidation of the alcohols of Formula III with a variety of reagents (Scheme 2). The oxidation of alcohols to carbonyl compounds is well known in the art, see Larock (ibid., pp 604–613) for conditions and details. For the present invention, the most convenient reagent for the transformation is manganese dioxide. Simply stirring the reagent with a compound of Formula IX at 25° C. to 115° C. accomplishes the oxidation. The manganese dioxide is used in excess (typically 3–10 fold excess). Many solvents may be used such as aromatic hydrocarbons and halogenated hydrocarbons.

Scheme 2

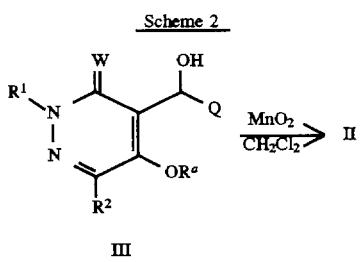

The alcohols of Formula III are obtained by the reaction of a lithiopyridazinone with a substituted aldehyde of Formula V (Scheme 3). The lithiopyridazinone is obtained by the reaction of an alkyllithium with a halogenated pyridazinone of Formula IV. The lithiation may be aided by the addition of tetramethylethylenediamine (TMEDA) and is carried out at a low temperature from −40° C. to −78° C. The preferred solvent for the reaction is tetrahydrofuran and the preferred base is n-butyllithium. The aldehyde is added to the reaction mixture after the formation of the lithium reagent and allowed to warm to ambient temperature to complete the reaction.

Scheme 3

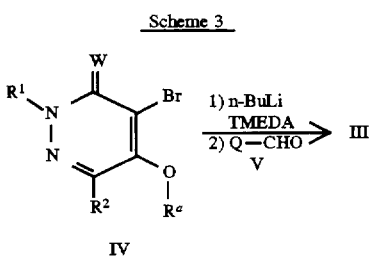

A generally useful method for synthesizing the alkoxy pyridazinones of Formula IV containing a halogen is by displacement of one halogen in 4,5-dihalogenated pyridazinones with an alkoxide as shown in Scheme 4. Details and references for this process can be found in Dury, Angew. Chem., Internal. Edit., 4, 292–300 (1965). Typically, the dihalopyridazinone of Formula VI is dissolved in the alcohol and treated with a solution of the alkoxide at room temperature. Only one halogen is displaced under these conditions.

Scheme 4

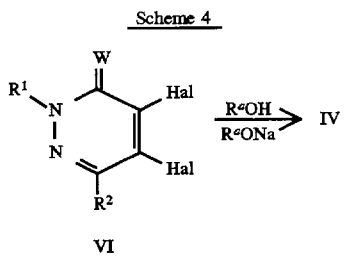

Some dihalopyridazinones are commercially available and many others are known in the art (See Dury, ibid.). Other halopyridazinones of Formula VI can be synthesized by reaction of mucohalic or dihalomaleic anhydrides of Formula VII with hydrazine derivatives as shown in Scheme 5. The reaction is carried out in a stepwise fashion wherein a compound of Formula VII is allowed to react with the hydrazine to make a hydrazone. The pyridazinone is then obtained by heating the reaction in the presence of an acid catalyst. The reaction can be accelerated if it is run in the presence of a trap for water such as molecular sieves or when a Dean-Stark trap is used to azeotropically remove the water.

Scheme 5

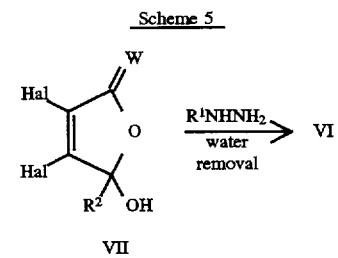

As shown in Scheme 6, compounds of Formula I (R$^3$=OH) can be converted to other compounds of the invention by acylation, sulfonylation, or alkylation. Acylation can be accomplished using commercially available acid halides or acids. In a similar sequence, sulfonyl halides can be reacted with the compounds of Formula I (R$^3$=OH) in tetrahydrofuran or dichloromethane in the presence of a base such as triethylamine to afford the sulfonylated compounds of Formula I. The alkylation of the hydroxyl group can be accomplished by reaction of alkyl halides or sulfonates in the presence of an acid acceptor. The acid acceptor can be an alkali hydride, carbonate, or hydroxide. Preferred solvents include dimethylformamide, dimethylacetamide, or acetonitrile. Normally the reaction will proceed at room temperature but may also be carried out at more elevated temperatures if necessary.

Scheme 6

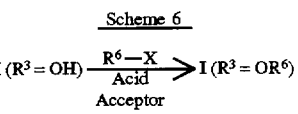

X = leaving group such as Cl, Br, I, or (halo)alkylsulfonate

Halogenation can be accomplished by reaction of a compound of Formula I (R$^3$=OH) with a halogenating reagent to give a compound of Formula I (R$^3$=halogen) as shown in Scheme 7. Thionyl chloride, phosphorus oxychloride, phosphorus tribromide and phosphorus pentachloride can all be used for introduction of a halogen. The compound of Formula I ($R^3$=OH) and a large excess of the halogenating reagent are allowed to react at between 25° C. to 150° C. The reaction may be carried out without a solvent or with an inert solvent such as toluene, benzene, or dichloromethane. A compendium of methods for halogenation of pyridazinones may be found in *Advances in Heterocyclic Chemistry*, Vol. 8, (loc. cit., pp 249–252).

Scheme 7

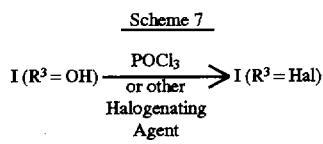

As shown in Scheme 8, halogenated compounds of Formula I may be converted to other compounds of the invention. For example, reaction with sulfur nucleophiles such as sodium hydrogen sulfide or sodium methylmercaptide will introduce a sulfur substituent. Using conditions described for Scheme 4, alkoxides may be introduced. The sulfur containing compounds of Formula I may be oxidized to sulfoxides and sulfones using a variety of reagents and conditions. Very conveniently, hydrogen peroxide may be used in conjunction with lower alkanoic acids to perform the oxidation. In order to obtain the sulfoxides (m=1), shorter reaction times and smaller excesses of peroxide are used. Other reagents which may be used for the oxidation are Oxone® and sodium periodate. A compendium of methods for the oxidation of sulfides to sulfoxides and sulfones can be found in Oae, *The Organic Chemistry of Sulfur* (Plenum: New York, 1979). See also Patai and Rappoport, Eds., *The Syntheses of Sulphones, Sulphoxides and Cyclic Sulphides* (Wiley, Chichester, 1994).

Scheme 8

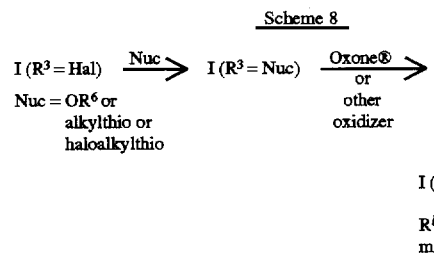

Intermediate aldehydes of Formula V can be made from the known acids, esters, and acid chlorides of Formulae VIII or IX by reduction procedures (e.g., using diisobutylaluminum hydride (DiBAH)) known in the literature: See Larock, loc. cit., pp 619–625 for typical procedures and conditions.

Scheme 9

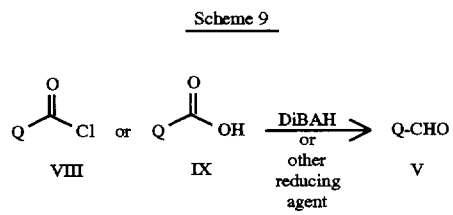

Aldehydes of Formula V can also be obtained by the reaction of Grignard or lithium species with formylating reagents. Typically the Grignard or lithium species is prepared from a known bromide or iodide of Formula X and then treated with dimethylformamide at low temperature from −40° C. to −78° C.

Scheme 10

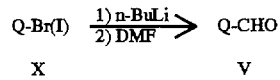

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane.

Intermediate 1

4-Bromo-5-methoxy-2-methyl-3(2H)-pyridazinone 4,5-Dibromo-2-methyl-3(2H)-pyridazinone (20 g, Maybridge Chemical Company) was cooled in an ice bath and treated successively with methanol (200 mL) and sodium methoxide (12 mL of a 30% solution in methanol). The ice bath was removed and the reaction was allowed to stir at 23° C. for 3 h. The methanol was removed by evaporation at reduced pressure. The residue was partitioned between dichloromethane and water. The organic layer was dried over magnesium sulfate and concentrated to provide the desired product 17 g as a whim solid melting at 146°–147° C. $^1$H NMR (CDCl$_3$): 7.7 (1H), 4.0 (3H), 3.8 (3H).

Intermediate 2

3,4-Dihydro-4,4,5,8-tetramethyl-2H-1-benzothiopyran-6-carboxaldehyde

6-Bromo-3,4-dihydro-4,4,5,8-tetramethyl-2H-1-benzothiopyran (19.8 g, World Patent Application 95/04054) was dissolved in diethyl ether (350 mL) and treated with n-butyllithium (2.5N in hexanes, 42 mL). The mixture was stirred at room temperature for 1 h and then cooled in a dry-ice/acetone bath. Dimethylformamide (16 mL) was added over a period of several minutes and the reaction bath was allowed to warm to −40° C. Hydrochloric acid (1N aqueous, 100 mL) was added and the mixture was allowed to warm to 23° C. The organic phase was separated and washed with saturated aqueous sodium bicarbonate solution (100 mL). The organic phase was dried over magnesium sulfate, filtered, and evaporated under reduced pressure. The residue was subjected to chromatography on silica gel using hexanes/ether (9:1) as eluent to afford the desired compound as a yellow semi-solid (7.7 g). $^1$H NMR(CDCl$_3$): δ 1.5 (6H), 2.0 (2H), 2.3 (3H), 2.8 (3H), 3.0 (2H), 7.4 (1H), 10.2 (1H).

EXAMPLE 1

4-[(3,4-Dihydro-4,4,5,8-tetramethyl-2H-1-benzothiopyran-6-yl)carbonyl]-5-methoxy-2-methyl-3 (2H)-pyridazinone Intermediate 1 (2.6 g) was dissolved in tetrahydrofuran (250 mL) and treated with tetramethylethylenediamine (2.6 mL). The solution was then cooled in a dry-ice/acetone bath and watched carefully. At −40° C., the solution began to become slightly cloudy and n-butyllithium (6.5 mL, 2.5 N in hexanes) was added quickly over 1 minute. The blue-black mixture was stirred for 15 min with cooling. Intermediate 2 (3.4 g) was added as a solid and the mixture was allowed to warm to room temperature. Stirring was continued for 66 h. A solution of saturated aqueous ammonium chloride (100 mL) was added followed by diethyl ether (300 mL). The layers were separated and the aqueous layer was extracted with dichloromethane (200 mL). The organic layers were dried over magnesium sulfate and evaporated under reduced pressure and the residue was subjected to chromatography on silica gel using hexanes/ethyl acetate (3:1 to 1.5:1) as eluent to afford a red foam (2.56 g). The foam was dissolved in dichloromethane (100 mL) and treated with activated manganese dioxide (20 g). The mixture was heated at reflux for 2 h, cooled and filtered through Celite®. The solvent was removed under reduced pressure to give a crude oil (2.35 g) containing the title compound of Example 1, a compound of the invention. $^1$H NMR (CDCl$_3$): δ 5 1.5 (6H), 2.0 (2H), 2.2 (3H), 2.8 (3H), 2.9 (2H), 3.8 (3H), 3.9 (3H), 7.1 (1H), 7.8 (1H).

EXAMPLE 2

4-[(3,4-Dihydro-4,4,5,8-tetramethyl-2H-1-benzothiopyran-6-yl)carbonyl]-5-methoxy-2-methyl-3(2H)-pyridazinone S,S-dioxide The title compound of Example 1 (2.3 g) was dissolved in acetone (5 mL) and treated with a solution of Oxone® (5.3 g) in water (30 mL). The yellow suspension was stirred at 23° C. for 30 min. Aqueous sodium bisulfite solution (100 mL of 15%) was added followed by dichloromethane (100 mL). The layers were separated and the organic layer was dried with magnesium sulfate and concentrated under reduced pressure. The residue was subjected to chromatography on silica gel using hexanes/ethyl acetate (2:1) to ethyl acetate as eluent to afford the title compound of Example 2, a compound of the invention, as a white solid (1.8 g) melting at 201°–203° C. $^1$H NMR (CDCl$_3$): δ 1.6 (6H), 2.4 (2H), 2.69 (3H), 2.73 (3H), 3.4 (2H), 3.7 (3H), 4.0 (3H), 7.1(1H), 7.9 (1H).

EXAMPLE 3

4-[(3,4-Dihydro-4,4,5,8-tetramethyl-2H-1-benzothiopyran-6-yl)carbonyl]-5-hydroxy-2-methyl-3(2H)-pyridazinone S,S-dioxide The title compound of Example 2 (1.55 g) was dissolved in dichloromethane (80 mL) and treated with boron tribromide (1.0M in dichloromethane, 10 mL). The solution turned red-brown and was heated to reflux for 1 min and allowed to stir at 23° C. for 3.5 h. A tarry solid was noted and the liquid was decanted from it. The solid was treated with aqueous hydrochloric acid (1N, 50 mL) and ethyl acetate (100 mL). The organic layer was separated, dried over magnesium sulfate and concentrated under reduced pressure. The residue was triturated with ether to afford the title compound of Example 3, a compound of the invention, as a white solid (1.4 g) melting at 241°–243° C. $^1$H NMR (CDCl$_3$): δ 1.5 (6H), 2.3 (2H), 2.4 (3H), 2.7 (3H), 3.4 (2H), 3.6 (3H), 6.8 (1H), 7.7 (1H), 14.2 (1H).

EXAMPLE 4

4-[(3,4-Dihydro-4,4,5,8-tetramethyl-2H-1-benzothiopyran-6-yl)carbonyl]-2-methyl-5-[(phenylsulfonyloxy]-3(2H)-pyridazinone S,S-dioxide The tire compound of Example 3 (0.4 g) was dissolved in tetrahydrofuran (15 mL) and treated sequentially with triethylamine (0.15 mL) and benzenesulfonyl chloride (0.15 mL). The mixture was stirred at 23° C. for 18 h. The solvent was evaporated and the residue was partitioned between water (30 mL) and dichloromethane (30 mL). the dichloromethane layer was dried over magnesium sulfate and concentrated under reduced pressure. The resulting residue was subjected to chromatography on silica gel using hexanes/ethyl acetate (1:1 to 1:2) as eluent to afford the title compound of Example 4, a compound of the invention, as a white solid (0.45 g) melting at 88°–91° C. $^1$H NMR (CDCl$_3$): δ 1.5 (6H), 2.3 (2H), 2.6 (3H), 2.7 (3H), 3.4 (2H), 3.7 (3H), 6.9–8.1 (7H).

EXAMPLE 5

5-Chloro-4-[(3,4-dihydro-4,4,5,8-tetramethyl-2H-1-benzothiopyran-6-yl)carbonyl]-2-methyl-3(2H)-pyridazinone S,S-dioxide The title compound of Example 3 (0.25 g) was heated with thionyl chloride (6 mL) at reflux for 5 h. The volatiles were removed under reduced pressure and the residue was partitioned between dichloromethane and saturated aqueous sodium bicarbonate. The organic layer was dried over magnesium sulfate and evaporated under reduced pressure. The residue was subjected to chromatography using hexanes/ethyl acetate (2:1) to give the title compound of Example 5, a compound of the invention, as a white solid (0.1 g) melting at 205°–207° C. $^1$H NMR (CDCl$_3$): δ 1.6 (6H), 2.4 (2H), 2.7 (6H), 3.4 (2H), 3.8 (3H), 7.1 (1H), 7.9 (1H).

By the procedures described herein together with methods known in the art, the following compounds of Tables 1–5 can be prepared. The following abbreviations are used in the Tables which follow: t=tertiary, n=normal, c=cyclo, Me=methyl, Et=ethyl, Pr=propyl, Bu=butyl, Ph=phenyl, OMe=methoxy, SMe=methylthio, SEt=ethylthio, CN=cyano, NO$_2$=nitro, S(O)Me=methylsulfinyl, SO$_2$Me=methylsulfonyl, SO2Et=ethylsulfonyl, CO$_2$Me=methoxycarbonyl, CO$_2$Et=ethoxycarbonyl, and p-Tol=4-methylphenyl.

TABLE 1

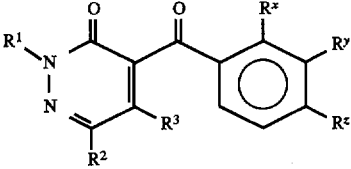

$R^1 = Me, R^2 = H, R^3 = OH$ and

| $R^x$ | $R^y$ | $R^z$ | $R^x$ | $R^y$ | $R^z$ |
|---|---|---|---|---|---|
| Me | H | SO₂Me | SO₂Me | H | CF₃ |
| CF₃ | H | SO₂Me | SO₂Me | H | Me |
| OMe | H | SO₂Me | SO₂Me | H | OMe |
| Cl | H | SO₂Me | SO₂Me | H | Cl |
| Br | H | SO₂Me | SO₂Me | H | Br |
| I | H | SO₂Me | SO₂Me | H | I |
| OCF₃ | H | SO₂Me | SO₂Me | H | OCF₃ |
| O-c-pentyl | H | SO₂Me | SO₂Me | H | OSO₂Me |
| OSO₂Me | H | SO₂Me | SO₂Me | H | CO₂Me |
| OCOCH₃ | H | SO₂Me | SO₂Me | H | CN |
| OCO₂Et | H | SO₂Me | SO₂Me | H | NO₂ |
| OCH₂CN | H | SO₂Me | SO₂Et | H | CF₃ |
| OCH₂CH₂OMe | H | SO₂Me | SO₂Et | H | Me |
| SO₂Me | H | SO₂Me | SO₂Et | H | OMe |
| SO₂NMe₂ | H | SO₂Me | SO₂Et | H | Cl |
| COCH₃ | H | SO₂Me | SO₂Et | H | Br |
| COCF₃ | H | SO₂Me | SO₂Et | H | OCF₃ |
| CO₂Me | H | SO₂Me | SO₂Et | H | OSO₂Me |
| CO₂Et | H | SO₂Me | SO₂Et | H | CN |
| CONMe₂ | H | SO₂Me | SO₂Et | H | NO₂ |
| CONHMe | H | SO₂Me | NO₂ | H | Cl |
| CONHPh | H | SO₂Me | NO₂ | H | CF₃ |
| NMe₂ | H | SO₂Me | NO₂ | H | Me |
| NHPh | H | SO₂Me | NO₂ | H | OMe |
| CN | H | SO₂Me | NO₂ | H | CN |
| NO₂ | H | SO₂Me | NO₂ | H | Br |
| Me | H | NO₂ | NO₂ | H | I |
| CF₃ | H | NO₂ | Cl | H | SO₂Et |
| Cl | H | NO₂ | Cl | H | SO₂-n-Pr |
| Br | H | NO₂ | Cl | H | SEt |
| CN | H | NO₂ | Cl | H | SO₂CF₃ |
| Cl | H | Cl | Cl | H | S(O)Me |
| Cl | H | Br | Cl | H | SCF₃ |
| Cl | H | CF₃ | Cl | CO₂Me | SO₂Me |
| Cl | H | I | Cl | CO₂Me | SO₂Et |
| Cl | H | CN | Cl | OCH₂CH₂OMe | SO₂Me |
| Cl | Cl | Cl | Cl | OCH₂CH₂OMe | SO₂Et |
| Cl | OMe | SO₂Me | CF₃ | OCH₂CH₂OMe | SO₂Me |
| Cl | Cl | NO₂ | CF₃ | CO₂Me | SO₂Me |
| Cl | OMe | NO₂ | Cl | CO₂Et | SO₂Me |
| Cl | OCH₂CH₂OMe | Cl | Cl | OMe | Cl |
| Me | CO₂Me | SO₂Me | Me | CO₂Me | SO₂Et |

TABLE 2

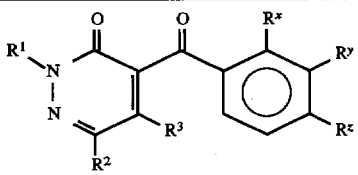

$R^1 = Et, R^2 = H, R^3 = OH$ and

| $R^x$ | $R^y$ | $R^z$ | $R^x$ | $R^y$ | $R^z$ |
|---|---|---|---|---|---|
| Me | H | SO₂Me | SO₂Me | H | CF₃ |
| CF₃ | H | SO₂Me | SO₂Me | H | Me |
| OMe | H | SO₂Me | SO₂Me | H | OMe |
| Cl | H | SO₂Me | SO₂Me | H | Cl |
| Br | H | SO₂Me | SO₂Me | H | Br |
| I | H | SO₂Me | SO₂Me | H | I |
| OCF₃ | H | SO₂Me | SO₂Me | H | OCF₃ |
| O-c-pentyl | H | SO₂Me | SO₂Me | H | OSO₂Me |

TABLE 2-continued

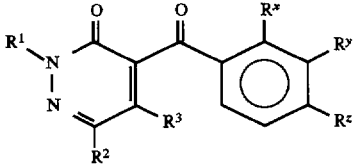

$R^1 = Et, R^2 = H, R^3 = OH$ and

| $R^x$ | $R^y$ | $R^z$ | $R^x$ | $R^y$ | $R^z$ |
|---|---|---|---|---|---|
| $OSO_2Me$ | H | $SO_2Me$ | $SO_2Me$ | H | $CO_2Me$ |
| $OCOCH_3$ | H | $SO_2Me$ | $SO_2Me$ | H | CN |
| $OCO_2Et$ | H | $SO_2Me$ | $SO_2Me$ | H | $NO_2$ |
| $OCH_2CN$ | H | $SO_2Me$ | $SO_2Et$ | H | $CF_3$ |
| $OCH_2CH_2OMe$ | H | $SO_2Me$ | $SO_2Et$ | H | Me |
| $SO_2Me$ | H | $SO_2Me$ | $SO_2Et$ | H | OMe |
| $SO_2N(Me)_2$ | H | $SO_2Me$ | $SO_2Et$ | H | Cl |
| $COCH_3$ | H | $SO_2Me$ | $SO_2Et$ | H | Br |
| $COCF_3$ | H | $SO_2Me$ | $SO_2Et$ | H | $OCF_3$ |
| $CO_2Me$ | H | $SO_2Me$ | $SO_2Et$ | H | $OSO_2Me$ |
| $CO_2Et$ | H | $SO_2Me$ | $SO_2Et$ | H | CN |
| $CONMe_2$ | H | $SO_2Me$ | $SO_2Et$ | H | $NO_2$ |
| CONHMe | H | $SO_2Me$ | $NO_2$ | H | Cl |
| CONHPh | H | $SO_2Me$ | $NO_2$ | H | $CF_3$ |
| $NMe_2$ | H | $SO_2Me$ | $NO_2$ | H | Me |
| NHPh | H | $SO_2Me$ | $NO_2$ | H | OMe |
| CN | H | $SO_2Me$ | $NO_2$ | H | CN |
| $NO_2$ | H | $SO_2Me$ | $NO_2$ | H | Br |
| Me | H | $NO_2$ | $NO_2$ | H | I |
| $CF_3$ | H | $NO_2$ | Cl | H | $SO_2Et$ |
| Cl | H | $NO_2$ | Cl | H | $SO_2$-n-Pr |
| Br | H | $NO_2$ | Cl | H | SEt |
| CN | H | $NO_2$ | Cl | H | $SO_2CF_3$ |
| Cl | H | Cl | Cl | H | S(O)Me |
| Cl | H | Br | Cl | H | $SCF_3$ |
| Cl | H | $CF_3$ | Cl | $CO_2Me$ | $SO_2Me$ |
| Cl | H | I | Cl | $CO_2Me$ | $SO_2Et$ |
| Cl | H | CN | Cl | $OCH_2CH_2OMe$ | $SO_2Me$ |
| Cl | Cl | Cl | Cl | $OCH_2CH_2OMe$ | $SO_2Et$ |
| Cl | OMe | $SO_2Me$ | $CF_3$ | $OCH_2CH_2OMe$ | $SO_2Me$ |
| Cl | Cl | $NO_2$ | $CF_3$ | $CO_2Me$ | $SO_2Me$ |
| Cl | OMe | $NO_2$ | Cl | $CO_2Et$ | $SO_2Me$ |
| Cl | $OCH_2CH_2OMe$ | Cl | Cl | OMe | Cl |
| Me | $CO_2Me$ | $SO_2Me$ | Me | $CO_2Me$ | $SO_2Et$ |

TABLE 3

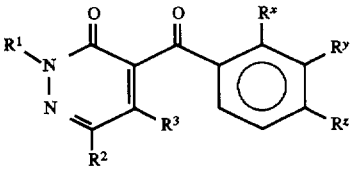

| $R^1$ | $R^2$ | $R^3$ | $R^x$ | $R^y$ | $R^z$ | $R^1$ | $R^2$ | $R^3$ | $R^x$ | $R^y$ | $R^z$ |
|---|---|---|---|---|---|---|---|---|---|---|---|
| Me | H | $OCOCH_3$ | $SO_2Me$ | H | $CF_3$ | Me | H | $SCF_3$ | $SO_2Me$ | H | $CF_3$ |
| Me | H | $OSO_2Me$ | $SO_2Me$ | H | $CF_3$ | Me | H | $S(O)CF_3$ | $SO_2Me$ | H | $CF_3$ |
| Me | H | $OSO_2Ph$ | $SO_2Me$ | H | $CF_3$ | Me | H | $SO_2CF_3$ | $SO_2Me$ | H | $CF_3$ |
| Me | H | OMe | $SO_2Me$ | H | $CF_3$ | Me | H | SH | $SO_2Me$ | H | $CF_3$ |
| Me | H | $OCH_2OMe$ | $SO_2Me$ | H | $CF_3$ | Et | H | $OSO_2Ph$ | $SO_2Me$ | H | $CF_3$ |
| Me | H | OCOPh | $SO_2Me$ | H | $CF_3$ | $CF_3CH_2$ | H | OH | $SO_2Me$ | H | $CF_3$ |
| Me | H | $OCH_2OEt$ | $SO_2Me$ | H | $CF_3$ | allyl | H | OH | $SO_2Me$ | H | $CF_3$ |
| Me | H | $OCO_2Et$ | $SO_2Me$ | H | $CF_3$ | 2-Cl-allyl | H | OH | $SO_2Me$ | H | $CF_3$ |
| Me | H | $OSO_2CF_3$ | $SO_2Me$ | H | $CF_3$ | propargyl | H | OH | $SO_2Me$ | H | $CF_3$ |
| Me | H | $OSO_2$-p-Tol | $SO_2Me$ | H | $CF_3$ | 3-Cl-propargyl | H | OH | $SO_2Me$ | H | $CF_3$ |
| Me | H | Cl | $SO_2Me$ | H | $CF_3$ | c-pentyl | H | OH | $SO_2Me$ | H | $CF_3$ |
| Me | H | Br | $SO_2Me$ | H | $CF_3$ | Me | Me | OH | $SO_2Me$ | H | $CF_3$ |
| Me | H | SMe | $SO_2Me$ | H | $CF_3$ | Me | $CF_3$ | OH | $SO_2Me$ | H | $CF_3$ |
| Me | H | $SO_2Me$ | $SO_2Me$ | H | $CF_3$ | Me | Cl | OH | $SO_2Me$ | H | $CF_3$ |
| Me | H | S(O)Me | $SO_2Me$ | H | $CF_3$ | Me | Br | OH | $SO_2Me$ | H | $CF_3$ |

TABLE 3-continued

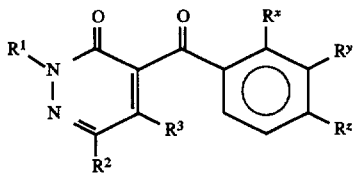

| R¹ | R² | R³ | Rˣ | Rʸ | Rᶻ |
|---|---|---|---|---|---|
| Me | OMe | OH | SO₂Me | H | CF₃ |
| Me | Et | OH | SO₂Me | H | CF₃ |
| Me | H | OSO₂Ph | SO₂Me | H | Cl |
| Me | H | OSO₂Ph | Cl | H | SO₂Me |
| Me | H | OSO₂Ph | Cl | CO₂Me | SO₂Me |
| Me | H | OSO₂Ph | Cl | CO₂Me | SO₂Et |
| Me | H | OSO₂Ph | Cl | OCH₂CH₂OMe | SO₂Me |
| Me | H | OSO₂Ph | CF₃ | H | SO₂Me |
| Me | H | OSO₂Ph | CF₃ | H | SO₂Et |
| Me | H | OSO₂Me | Cl | CO₂Me | SO₂Me |
| Me | H | OSO₂Me | Cl | OCH₂CH₂OMe | SO₂Me |
| Me | H | OSO₂Ph | Me | CO₂Me | SO₂Me |

TABLE 4

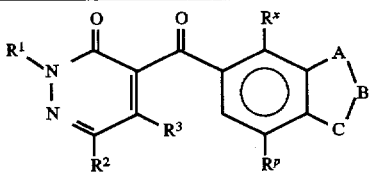

R¹ = Me, R² = H, R³ = OH and

| Rˣ | Rᵖ | A | B | C |
|---|---|---|---|---|
| Me | Me | CMe₂ | (CH₂)₂ | SO₂ |
| Me | H | CMe₂ | (CH₂)₂ | SO₂ |
| Cl | Cl | CMe₂ | (CH₂)₂ | SO₂ |
| Cl | H | CMe₂ | (CH₂)₂ | SO₂ |
| Me | Me | CH₂ | CH₂ | SO₂ |
| Me | H | CH₂ | CH₂ | SO₂ |
| Me | Me | CH₂ | (CH₂)₂ | SO₂ |
| Me | H | CH₂ | (CH₂)₂ | SO₂ |
| SO₂Me | H | O | CF₂ | O |
| Me | Me | CH₂ | CMe₂ | O |
| Me | H | CH₂ | CMe₂ | O |
| Cl | H | CO | N—Me | SO₂ |
| Me | H | CO | N—Me | SO₂ |
| Cl | H | CO | N-t-Bu | SO₂ |
| Me | Me | C=NOMe | (CH₂)₂ | SO₂ |
| Me | H | C=NOMe | (CH₂)₂ | SO₂ |
| Me | Me | CH=CH | CH₂ | O |
| Me | H | CH=CH | CH₂ | O |
| Cl | H | O | (CH₂)₂ | O |
| Cl | H | O | CH₂ | O |
| SO₂Me | H | O | (CH₂)₂ | O |
| SO₂Me | H | O | CH₂ | O |
| SO₂Me | H | O | (CH₂)₂ | CH₂ |
| SO₂Me | H | S | (CH₂)₂ | CH₂ |
| SO₂Me | H | SO₂ | (CH₂)₂ | CH₂ |
| SO₂Me | H | CO | N—Me | CH₂ |
| SO₂Me | H | CO | N-t-Bu | CH₂ |
| SO₂Me | H | CO | N—Me | (CH₂)₂ |
| SO₂Me | H | CO | N-t-Bu | (CH₂)₂ |
| SO₂Me | H | CO | N—Me | CH=CH |
| SO₂Me | H | CO | N-t-Bu | CH=CH |
| SO₂Me | H | CH₂ | CH₂ | CH₂ |
| SO₂Me | H | CH₂ | (CH₂)₂ | CH₂ |
| Me | Me | O | (CH₂)₂ | SO₂ |

TABLE 4-continued

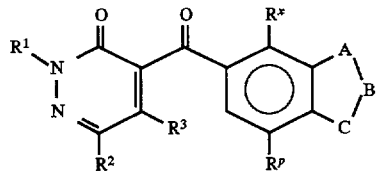

R¹ = Me, R² = H, R³ = OH and

| Rˣ | Rᵖ | A | B | C |
|---|---|---|---|---|
| Cl | Cl |  | (CH₂)₂ | SO₂ |

TABLE 5

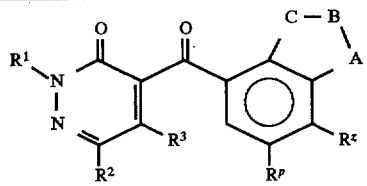

R¹ = Me, R² = H, R³ = OH and

| Rᶻ | Rᵖ | A | B | C |
|---|---|---|---|---|
| Me | Me | CMe₂ | (CH₂)₂ | SO₂ |
| Me | H | CMe₂ | (CH₂)₂ | SO₂ |
| Cl | Cl | CMe₂ | (CH₂)₂ | SO₂ |
| Cl | H | CMe₂ | (CH₂)₂ | SO₂ |
| Me | Me | CH₂ | CH₂ | SO₂ |
| Me | H | CH₂ | CH₂ | SO₂ |
| Me | Me | CH₂ | (CH₂)₂ | SO₂ |
| Me | H | CH₂ | (CH₂)₂ | SO₂ |
| SO₂Me | H | O | CF₂ | O |
| Me | Me | CH₂ | CMe₂ | O |
| Me | H | CH₂ | CMe₂ | O |
| Cl | H | CO | N—Me | SO₂ |
| Me | H | CO | N—Me | SO₂ |
| Cl | H | CO | N-t-Bu | SO₂ |
| Me | Me | C=NOMe | (CH₂)₂ | SO₂ |
| Me | H | C=NOMe | (CH₂)₂ | SO₂ |
| Me | Me | CH=CH | CH₂ | O |
| Me | H | CH=CH | CH₂ | O |
| Cl | H | O | (CH₂)₂ | O |
| Cl | H | O | CH₂ | O |
| SO₂Me | H | O | (CH₂)₂ | O |
| SO₂Me | H | O | CH₂ | O |
| SO₂Me | H | O | (CH₂)₂ | CH₂ |
| SO₂Me | H | S | (CH₂)₂ | CH₂ |
| SO₂Me | H | SO₂ | (CH₂)₂ | CH₂ |
| SO₂Me | H | CO | N—Me | CH₂ |
| SO₂Me | H | CO | N-t-Bu | CH₂ |
| SO₂Me | H | CO | N—Me | (CH₂)₂ |
| SO₂Me | H | CO | N-t-Bu | (CH₂)₂ |
| SO₂Me | H | CO | N—Me | CH=CH |
| SO₂Me | H | CO | N-t-Bu | CH=CH |
| SO₂Me | H | CH₂ | CH₂ | CH₂ |
| SO₂Me | H | CH₂ | (CH₂)₂ | CH₂ |
| Me | Me | O | (CH₂)₂ | SO₂ |

TABLE 5-continued

R¹ = Me, R² = H, R³ = OH and

| R$^x$ | R$^p$ | A | B | C |
|---|---|---|---|---|
| Cl | Cl | O⟨ ⟩O (dioxolane) | (CH$_2$)$_2$ | SO$_2$ |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et at., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylatect alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147–48, *Perry's Chemical Engineer's Handbook*, 4th Ed., McGraw-Hill, New York, 1963, pages 8—57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, 1961, pp 81–96; and Hance et at., *Weed Control Handbook*, 8th Ed., Blackwell Scientific Publications, Oxford, 1989.

In the following Examples, all percentages are by weight and all formulations are prepared in conventional ways. Compound numbers refer to compounds in Index Tables A–C.

| Example A | |
|---|---|
| High Strength Concentrate | |
| Compound 14 | 98.5% |
| silica aerogel | 0.5% |
| synthetic amorphous fine silica | 1.0%. |

-continued

Example B

Wettable Powder

| | |
|---|---|
| Compound 14 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example C

Granule

| | |
|---|---|
| Compound 14 | 10.0% |
| attapulgite granules (low volatile matter, 0.71/0.30 mm; U.S.S. No. 25–50 sieves) | 90.0%. |

Example D

Extruded Pellet

| | |
|---|---|
| Compound 14 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Test results indicate that the compounds of the present invention are highly active preemergent and postemergent herbicides or plant growth regulants. Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Some of the compounds will be useful for the control of selected grass and broadleaf weeds with tolerance to important agronomic crops which include but are not limited to barley, cotton, wheat, rape, sugar beets, corn (maize), soybeans, rice, tomato, potato, and plantation crops including coffee, cocoa, oil palm, rubber, sugarcane, citrus, grapes, fruit trees, nut trees, banana, plantain, pineapple, hops, tea, forests such as eucalyptus and conifers, e.g., loblolly pine, and turf species, e.g., Kentucky bluegrass, St. Augustine grass, Kentucky fescue and Bermuda grass. Those skilled in the art will appreciate that not all compounds are equally effective against all weeds. Alternatively, the subject compounds are useful to modify plant growth.

Compounds of this invention can be used alone or in combination with other commercial herbicides, insecticides or fungicides. Compounds of this invention can also be used in combination with commercial herbicide safeners such as benoxacor, dichlormid and furilazole to increase safety to certain crops. A mixture of one or more of the following herbicides with a compound of this invention may be particularly useful for weed control: acetochlor, acifluorfen and its sodium salt, aclonifen, acrolein (2-propenal), alachlor, ametryn, amidosulfuron, amitrole, ammonium sulfamate, anilofos, asulam, atrazine, azimsulfuron, benazolin, benazolin-ethyl, benfluralin, benfuresate, bensulfuron-methyl, bensulide, bentazone, bifenox, bromacil, bromoxynil, bromoxynil octanoate, butachlor, butralin, butylate, chlomethoxyfen, chloramben, chlorbromuron, chloridazon, chlorimuron-ethyl, chlornitrofen, chlorotoluron, chlorpropham, chlorsulfuron, chlorthal-dimethyl, cinmethylin, cinosulfuron, clethodim, clomazone, clopyralid, clopyralid-olamine, cyanazine, cycloate, cyclosulfamuron, 2,4-D and its butotyl, butyl, isoctyl and isopropyl esters and its dimethylammonium, diolamine and trolamine salts, dalmuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, 2-[4,5-dihydro-4-methyl-4-(1-methylethyl)-5-oxo-1H-imidazol-2-yl]-5-methyl-3-pyridinecarboxylic acid (AC 263,222), difenzoquat metilsulfate, diflufenican, dimepiperate, dimethenamid, dimethylarsinic acid and its sodium salt, dinitramine, diphenamid, diquat dibromide, dithiopyr, diuron, DNOC, endothal, EPTC, esprocarb, ethalfluralin, ethametsulfuron-methyl, ethofumesate, ethyl α,2-dichloro-5-[4-(difluoromethyl)-4,5-dihydro-3-methyl-5-oxo-1H-1,2,4-triazol-1-yl]-4-fluorobenzenepropanoate (F8426), fenoxaprop-ethyl, fenoxaprop-P-ethyl, fenuron, fenuron-TCA, tamprop-methyl, flamprop-M-isopropyl, flamprop-M-methyl, flazasulfuron, fluazifop-butyl, fluazifop-P-butyl, fluchloralin, flumetsulam, flumicloracpentyl, flumioxazin, fluometuron, fluoroglycofen-ethyl, flupoxam, fluridone, flurochloridone, fluroxypyr, fomesafen, fosamine-ammonium, glufosinate, glufosinate-ammonium, glyphosate, glyphosate-isopropylammonium, glyphosate-sesquisodium, glyphosate-trimesium, halosulfuron-methyl, haloxyfop-etotyl, haloxyfop-methyl, hexazinone, imazamethabenz-methyl, imazamox (AC 299 263), imazapyr, imazaquin, imazaquin-ammonium, imazethapyr, imazethapyr-ammonium, imazosulfuron, ioxynil, ioxynil octanoate, ioxynil-sodium, isoproturon, isouron, isoxaben, isoxaflutole (RPA 201772), lactofen, lenacil, linuron, maleic hydrazide, MCPA and its dimethylammonium, potassium and sodium salts, MCPA-isoctyl, mecoprop, mecoprop-P, mefenacet, mefluidide, metam-sodium, methabenzthiazuron, methyl [[2 -chloro-4-fluoro-5-[(tetrahydro-3-oxo-1H,3H-[1,3,4]thiadiazolo[3,4a] pyridazin-1-ylidene)amino]phenyl]thioacetate (KIH 9201), methylarsonic acid and its calcium, monoammonium, monosodium and disodium salts, methyl [[[1-[5-[2-chloro-4-(trifluoromethyl)phenoxy]-2-nitrophenyl]-2-methoxyethylidene]amino]oxy]acetate (AKH-7088), methyl 5-[[[[(4,6-dimethyl-2-pyrimidinyl)amino]carbonyl]amino]sulfonyl]-1-(2-pyridinyl)-1H-pyrazole-4-carboxylate (NC-330), metobenzuron, metolachlor, metosulam, metoxuron, metribuzin, metsulfuron-methyl, molinate, monolinuron, napropamide, naptalam, neburon, nicosulfuron, norflurazon, oryzalin, oxadiazon, 3-oxetanyl 2-[[[[(4,6-dimethyl-2-pyrimidinyl)amino]carbonyl]amino] sulfonyl]benzoate (CGA 277476), oxyfluorfen, paraquat dichloride, pebulate, pendimethilin, perfluidone, phenmedipham, picloram, picloram-potassium, pretilachlor, primisulfuron-methyl, prometon, prometryn, propachlor, propanil, propaquizafop, propazine, propham, propyzamide, prosulfuron, pyrazolynate, pyrazosulfuron-ethyl, pyridate, pyrithiobac, pyrithiobac-sodium, quinclorac, quizalofop-ethyl, quizalofop-P-ethyl, quizalofop-P-tefuryl, rimsulfuron, sethoxydim, siduron, simazine, sulcotrione (ICIA0051), sulfentrazone, sulfometuron-methyl, TCA, TCA-sodium, tebuthiuron, terbacil, terbuthylazine, terbutryn, thenylchlor, thiafluamide (BAY 11390), thifensulfuron-methyl, thiobericarb, tralkoxydim, tri-allate, triasulfuron, tribenuron-methyl, triclopyr, triclopyr-butotyl, triclopyr-triethylammonium, tridiphane, trifluralin, triflusulfuron-methyl, and vernolate.

In certain instances, combinations with other herbicides having a similar spectrum of control but a different mode of action will be particularly advantageous for preventing the development of resistant weeds.

A herbicidally effective amount of the compounds of this invention is determined by a number of factors. These factors include: formulation selected, method of application, amount and type of vegetation present, growing conditions, etc. In general, a herbicidally effective amount of compounds of this invention is 0.001 to 20 kg/ha with a preferred range of 0.004 to 1.0 kg/ha. One skilled in the art can easily determine the herbicidally effective amount necessary for the desired level of weed control.

The following Tests demonstrate the control efficacy of the compounds of this invention against specific weeds. The weed control afforded by the compounds is not limited, however, to these species. See Index Tables A-C for compound descriptions.

INDEX TABLE A

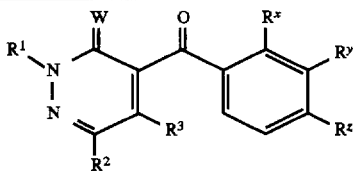

where $R^x$, $R^y$, and $R^z$ are $R^4$, and $R^5$ or H

| Cmpd No. | W | $R^1$ | $R^2$ | $R^3$ | $R^x$ | $R^y$ | $R^z$ | m.p.(°C.) |
|---|---|---|---|---|---|---|---|---|
| 1 | O | Me | H | OMe | H | H | F | 122–123 |
| 2 | O | t-Bu | H | OH | Cl | H | Cl | 208–209 |
| 3 | O | Me | H | OH | Cl | H | Cl | >250 |
| 4 | O | Et | H | OH | Cl | H | Cl | 175–177 |
| 5 | O | i-Pr | H | OH | Cl | H | Cl | 84–85 |
| 6 | O | Et | H | OMe | Cl | H | Cl | 118 |
| 7 | O | Me | H | OMe | F | H | F | 140–141 |
| 8 | O | Et | H | OH | $SO_2Me$ | H | $CF_3$ | oil* |
| 9 | O | Et | H | OMe | SMe | H | $CF_3$ | 120–122 |
| 10 | O | Me | H | OMe | Cl | H | F | 145–146 |
| 11 | O | Et | H | Cl | $SO_2Me$ | H | $CF_3$ | oil* |
| 12 | O | Et | H | $OSO_2Ph$ | $SO_2Me$ | H | $CF_3$ | oil* |
| 13 | O | Et | H | OMe | $SO_2Me$ | H | $CF_3$ | oil* |

*See Index Table C for $^1H$ NMR data.

INDEX TABLE B

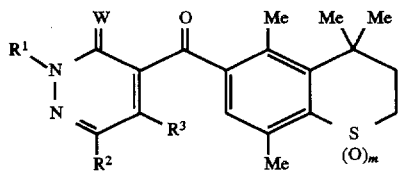

| Cmpd No. | W | $R^1$ | $R^2$ | $R^3$ | m | m.p:(°C.) |
|---|---|---|---|---|---|---|
| 14 (Ex. 3) | O | Me | H | OH | 2 | 241–243 |
| 15 (Ex. 4) | O | Me | H | $OSO_2Ph$ | 2 | 88–91 |
| 16 (Ex. 5) | O | Me | H | Cl | 2 | 205–207 |

INDEX TABLE B-continued

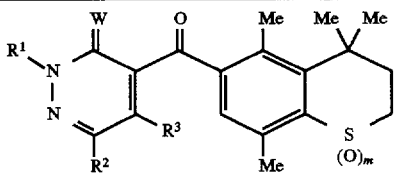

| Cmpd No. | W | $R^1$ | $R^2$ | $R^3$ | m | m.p.(°C.) |
|---|---|---|---|---|---|---|
| 17 | O | Me | H | $OSO_2Me$ | 2 | 220–222 |
| 18 (Ex. 2) | O | Me | H | OMe | 2 | 201–203 |
| 19 (Ex. 1) | O | Me | H | OMe | O | oil* |

*See Index Table C for 1H NMR data.

INDEX TABLE C

| Cmpd No. | $^1H$ NMR Data ($CDCl_3$ solution unless indicated otherwise)* |
|---|---|
| 8 | δ 13.5 (1H), 8.3 (1H), 7.9 (1H), 7.8 (1H), 7.4 (1H), 4.0 (2H), 3.2 (3H), 1.3 (3H). |
| 11 | δ 8.4 (1H), 7.9 (2H), 7.6 (1H), 4.2 (2H), 3.4 (3H), 1.4 (3H). |
| 12 | δ 8.2–7.5 (9H), 4.2 (2H), 3.3 (3H), 1.3 (3H). |
| 13 | δ 8.4 (1H), 7.9 (2H), 7.6 (1H), 4.2 (2H), 4.0 (3H), 3.3 (3H), 1.3 (3H). |
| 19 | δ 7.8 (1H), 7.1 (1H), 3.9 (3H), 3.8 (3H), 2.9 (2H), 2.8 (3H), 2.2 (3H), 2.0 (2H), 1.5 (6H). |

Test A

Seeds of barley (*Hordeurn vulgare*), barnyardgrass (*Echinochloa crus-galli*), bedstraw (*Galium aparine*), blackgrass (*Alopecurus myosuroides*), chickweed (*Stellaria media*), cocklebur (*Xanthium pensylvanicum*), corn (*Zea mays*), cotton (*Gossypium hirsutum*), crabgrass (*Digitaria sanguinalis*), downy brome (*Bromus tectorum*), giant foxtail (*Setaria faberii*), lambsquarters (*Chenopodium album*), morningglory (*Ipomoea hederacea*), rape (*Brassica napus*), rice (*Oryza sativa*), sorghum (*Sorghum bicolor*), soybean (*Glycine max*), sugar beet (*Beta vulgaris*), velvetleaf (*Abutlion theophrasti*), wheat (*Triticum aestivum*), wild buckwheat (*Polygonum convolvulus*), wild oat (*Avena fatua*) and purple nutsedge (*Cyperus rotundus*) tubers were planted and treated preemergence with test chemicals formulated in a non-phytotoxic solvent mixture which includes a surfactant.

At the same time, these crop and weed species were also treated with postemergence applications of test chemicals formulated in the same manner. Plants ranged in height from two to eighteen cm (one to four leaf stage) for postemergence treatments. Treated plants and controls were maintained in a greenhouse for twelve to sixteen days, after which all species were compared to controls and visually evaluated. Plant response ratings, summarized in Table A, are based on a scale of 0 to 10 where 0 is no effect and 10 is complete control. A dash (-) response means no test result.

TABLE A

| | COMPOUND | | | | COMPOUND | | |
|---|---|---|---|---|---|---|---|
| Rate 1000 g/ha | 8 | 14 | 15 | Rate 1000 g/ha | 8 | 14 | 15 |
| POSTEMERGENCE | | | | PREEMERGENCE | | | |
| Barley | 1 | 1 | 0 | Barley | 0 | 1 | 0 |
| Barnyardgrass | 9 | 9 | 9 | Barnyardgrass | 4 | 9 | 7 |
| Bedstraw | 9 | 7 | 5 | Bedstraw | 9 | 8 | 3 |
| Blackgrass | 2 | 2 | 0 | Blackgrass | 3 | 3 | 0 |
| Chickweed | 9 | 8 | 7 | Chickweed | 8 | 8 | 8 |
| Cocklebur | 9 | 9 | 8 | Cocklebur | 7 | 7 | 5 |

TABLE A-continued

| | | | | | | | | |
|---|---|---|---|---|---|---|---|---|
| Corn | 2 | 0 | 1 | Corn | 0 | 1 | 0 | |
| Cotton | 10 | 9 | 4 | Cotton | 6 | 4 | 0 | |
| Crabgrass | 7 | 9 | 8 | Crabgrass | 9 | 9 | 9 | |
| Downy brome | 2 | 1 | 0 | Downy brome | 5 | 1 | 0 | |
| Giant foxtail | 5 | 9 | 8 | Giant foxtail | 7 | 7 | 7 | |
| Lambsquarter | 9 | 9 | 9 | Lambsquarter | 9 | 9 | 10 | |
| Morningglory | 8 | 10 | 8 | Morningglory | 8 | 8 | 7 | |
| Nutsedge | 6 | 7 | 0 | Nutsedge | 10 | 5 | 2 | |
| Rape | 9 | 10 | 6 | Rape | 9 | 9 | 7 | |
| Rice | 8 | 9 | 7 | Rice | 9 | 10 | 8 | |
| Sorghum | 2 | 7 | 2 | Sorghum | 0 | 7 | 0 | |
| Soybean | 9 | 8 | 5 | Soybean | 6 | 7 | 6 | |
| Sugar beet | 9 | 10 | 10 | Sugar beet | 10 | 10 | 10 | |
| Velvetleaf | 10 | 9 | 8 | Velvetleaf | 10 | 9 | 10 | |
| Wheat | 5 | 2 | 0 | Wheat | 3 | 2 | 2 | |
| Wild buckwheat | 9 | 7 | 6 | Wild buckwheat | 8 | 8 | 7 | |
| Wild oat | 4 | 1 | 0 | Wild oat | 3 | 2 | 3 | |

| | COMPOUND | | | | | | COMPOUND | | | | |
|---|---|---|---|---|---|---|---|---|---|---|---|
| Rate 400 g/ha | 3 | 4 | 5 | 12 | 14 | Rate 400 g/ha | 3 | 4 | 5 | 12 | 14 |
| POSTEMERGENCE | | | | | | PREEMERGENCE | | | | | |
| Barley | 0 | 0 | 0 | 0 | 0 | Barley | 0 | 0 | 0 | 0 | 0 |
| Barnyardgrass | 2 | 1 | 0 | 9 | 9 | Barnyardgrass | 0 | 0 | 0 | 5 | 4 |
| Bedstraw | 8 | 0 | 0 | 7 | 7 | Bedstraw | — | 0 | 0 | 4 | 7 |
| Blackgrass | 4 | 2 | 0 | 0 | 2 | Blackgrass | 3 | 0 | 0 | 0 | 0 |
| Chickweed | 6 | 3 | 0 | 9 | 8 | Chickweed | 2 | 0 | 0 | 7 | 6 |
| Cocklebur | 2 | 0 | 0 | 6 | 9 | Cocklebur | 0 | 0 | 0 | 0 | 7 |
| Corn | 1 | 0 | 0 | 0 | 0 | Corn | 0 | 0 | 0 | 0 | 0 |
| Cotton | 2 | 2 | 0 | 9 | 7 | Cotton | 0 | 0 | 0 | 0 | 1 |
| Crabgrass | 3 | 6 | 0 | 0 | 9 | Crabgrass | 0 | 1 | 0 | 2 | 7 |
| Downy brome | 0 | 1 | 0 | 0 | 0 | Downy brome | 0 | 0 | 0 | 0 | 0 |
| Giant foxtail | 1 | 1 | 0 | 0 | 9 | Giant foxtail | 0 | 0 | 0 | 0 | 4 |
| Lambsquarter | 8 | 3 | 0 | 8 | 8 | Lambsquarter | 8 | 8 | 0 | 9 | 9 |
| Morningglory | 7 | 0 | 0 | 6 | 9 | Morningglory | 3 | 0 | 0 | 1 | 6 |
| Nutsedge | 0 | 0 | 0 | 0 | 5 | Nutsedge | 0 | 0 | — | 0 | 0 |
| Rape | 8 | 6 | 0 | 8 | 9 | Rape | 6 | 0 | 0 | 7 | 8 |
| Rice | 3 | 6 | 0 | 8 | 9 | Rice | 0 | 3 | 0 | 3 | 6 |
| Sorghum | 0 | 0 | 0 | 0 | 6 | Sorghum | 0 | 0 | 0 | 3 | 0 |
| Soybean | 2 | 2 | 0 | 5 | 8 | Soybean | 0 | 0 | 0 | 0 | 5 |
| Sugar beet | 10 | 6 | 0 | 8 | 10 | Sugar beet | 7 | 8 | 0 | 10 | 10 |
| Velvetleaf | 5 | 6 | 0 | 9 | 9 | Velvetleaf | 0 | 4 | 0 | 8 | 7 |
| Wheat | 1 | 0 | 0 | 4 | 1 | Wheat | 0 | 0 | 0 | 1 | 0 |
| Wild buckwheat | 6 | 2 | 0 | 8 | 7 | Wild buckwheat | 5 | 0 | 0 | 7 | 4 |
| Wild oat | 5 | 3 | 0 | 0 | 2 | Wild oat | 6 | 5 | 0 | 0 | 1 |

| | COMPOUND | | | | COMPOUND | | |
|---|---|---|---|---|---|---|---|
| Rate 200 g/ha | 8 | 14 | 15 | Rate 200 g/ha | 8 | 14 | 15 |
| POSTEMERGENCE | | | | PREEMERGENCE | | | |
| Barley | 1 | 0 | 0 | Barley | 0 | 0 | 0 |
| Barnyardgrass | 9 | 9 | 6 | Barnyardgrass | 0 | 3 | 1 |
| Bedstraw | 7 | 7 | 4 | Bedstraw | 4 | 1 | 3 |
| Blackgrass | 2 | 0 | 0 | Blackgrass | 2 | 0 | 0 |
| Chickweed | 8 | 7 | 4 | Chickweed | 8 | 3 | 5 |
| Cocklebur | 6 | 8 | 8 | Cocklebur | 3 | 1 | 0 |
| Corn | 0 | 0 | 0 | Corn | 0 | 0 | 0 |
| Cotton | 9 | 6 | 4 | Cotton | 2 | 0 | 0 |
| Crabgrass | 4 | 9 | 7 | Crabgrass | 1 | 4 | 9 |
| Downy brome | 0 | 0 | 0 | Downy brome | 0 | 0 | 0 |
| Giant foxtail | 2 | 9 | 6 | Giant foxtail | 0 | 3 | 2 |
| Lambsquarter | 9 | 8 | 9 | Lambsquarter | 9 | 9 | 9 |
| Morningglory | 7 | 8 | 6 | Morningglory | 4 | 2 | 0 |
| Nutsedge | 2 | 3 | 0 | Nutsedge | 10 | 0 | 0 |
| Rape | 7 | 9 | 5 | Rape | 8 | 1 | 3 |
| Rice | 7 | 9 | 6 | Rice | 6 | 7 | 7 |
| Sorghum | 0 | 5 | 0 | Sorghum | 0 | 0 | 0 |
| Soybean | 8 | 4 | 4 | Soybean | 5 | 5 | 2 |
| Sugar beet | 9 | 10 | 10 | Sugar beet | 10 | 10 | 9 |
| Velvetleaf | 10 | 9 | 7 | Velvetleaf | 10 | 6 | 8 |
| Wheat | 3 | 0 | 0 | Wheat | 0 | 0 | 0 |
| Wild buckwheat | 7 | 7 | 3 | Wild buckwheat | 4 | 0 | 0 |
| Wild oat | 2 | 0 | 0 | Wild oat | 0 | 0 | 0 |

TABLE A-continued

| Rate 100 g/ha | COMPOUND 3 | 4 | 5 | 12 | 14 | Rate 100 g/ha | COMPOUND 3 | 4 | 5 | 12 | 14 |
|---|---|---|---|---|---|---|---|---|---|---|---|
| POSTEMERGENCE | | | | | | PREEMERGENCE | | | | | |
| Barley | 0 | 0 | 0 | 0 | 0 | Barley | 0 | 0 | 0 | 0 | 0 |
| Barnyardgrass | 1 | 1 | 0 | 2 | 9 | Barnyardgrass | 0 | 0 | 0 | 0 | 1 |
| Bedstraw | 3 | 0 | 0 | 7 | 4 | Bedstraw | — | 0 | 0 | 2 | 0 |
| Blackgrass | 0 | 0 | 0 | 0 | 0 | Blackgrass | 0 | 0 | 0 | 0 | 0 |
| Chickweed | 1 | 0 | 0 | 9 | 1 | Chickweed | 2 | 0 | 0 | 0 | 0 |
| Cocklebur | 0 | 0 | 0 | 6 | 7 | Cocklebur | 0 | 0 | 0 | 0 | 0 |
| Corn | 0 | 0 | 0 | 0 | 0 | Corn | 0 | 0 | 0 | 0 | 0 |
| Cotton | 2 | 0 | 0 | 0 | 6 | Cotton | 0 | 0 | 0 | 0 | 0 |
| Crabgrass | 2 | 1 | 0 | 0 | 7 | Crabgrass | 0 | 0 | 0 | 0 | 2 |
| Downy brome | 0 | 0 | 0 | 0 | 0 | Downy brome | 3 | 0 | 0 | 0 | 0 |
| Giant foxtail | 0 | 0 | 0 | 0 | 7 | Giant foxtail | 0 | 0 | 0 | 0 | 1 |
| Lambsquarter | 3 | — | 0 | 9 | 8 | Lambsquarter | 3 | 0 | 0 | 8 | 9 |
| Morningglory | 2 | 0 | 0 | 0 | 8 | Morningglory | 0 | 0 | 0 | 0 | 0 |
| Nutsedge | 0 | 0 | 0 | 0 | 2 | Nutsedge | 0 | 0 | 0 | 0 | 0 |
| Rape | 4 | 0 | 0 | 7 | 9 | Rape | 0 | 0 | 0 | 4 | 0 |
| Rice | 0 | 0 | 0 | 3 | 9 | Rice | 0 | 0 | 0 | 0 | 7 |
| Sorghum | 0 | 0 | 0 | 0 | 3 | Sorghum | 0 | 0 | 0 | 0 | 0 |
| Soybean | 1 | 0 | 0 | 3 | 5 | Soybean | 0 | 0 | 0 | 0 | 2 |
| Sugar beet | 7 | 2 | 0 | 8 | 10 | Sugar beet | 4 | 0 | 0 | 9 | 10 |
| Velvetleaf | 5 | 0 | 0 | 8 | 8 | Velvetleaf | 0 | 0 | 0 | 4 | 5 |
| Wheat | 0 | 0 | 0 | 0 | 0 | Wheat | 3 | 0 | 0 | 0 | 0 |
| Wild buckwheat | 6 | 0 | 0 | 7 | 6 | Wild buckwheat | 3 | 0 | 0 | 0 | 0 |
| Wild oat | 0 | 0 | 0 | 0 | 2 | Wild oat | 3 | 3 | 0 | 0 | 0 |

Test B

Seeds of barnyardgrass (*Echinochloa crus-galli*), cocklebur (*Xanthium pensylvanicum*), crabgrass (Digitaria spp.), downy brome (*Bromus rectorum*), giant foxtail (*Setaria faberii*), morningglory (Ipomoea spp.), sorghum (*Sorghum bicolor*), velvetleaf (*Abutilon theophrasti*), and wild oat (*Avena fatua*) were planted into a sandy loam soil and sprayed preemergence (PRE) or treated by soil drench (PDRN), with test chemicals formulated in a non-phytotoxic solvent mixture which includes a surfactant. At the same time, these crop and weed species were also sprayed postemergence (POST) or sprayed to runoff (STRO), with test chemicals formulated in the same manner.

Plants ranged in height from two to eighteen cm and were in the two to three leaf stage for the postemergence treatment. Treated plants and untreated controls were maintained in a greenhouse for approximately eleven days, after which all treated plants were compared to untreated controls and visually evaluated for injury. Plant response ratings, summarized in Table B, are based on a 0 to 10 scale where 0 is no effect and 10 is complete control. A dash (-) response means no test results.

TABLE B

| Rate 2000 g/ha | COMPOUND 1 | 2 | 6 | 7 | 9 | 10 | 11 | Rate 1000 g/ha | COMPOUND 1 | 2 | 6 | 7 | 9 | 10 | 11 |
|---|---|---|---|---|---|---|---|---|---|---|---|---|---|---|---|
| PDRN | | | | | | | | STRO | | | | | | | |
| Barnyardgrass | 1 | 0 | 1 | 0 | 0 | 0 | 7 | Barnyardgrass | 1 | 0 | 1 | 0 | 0 | 0 | 4 |
| Cocklebur | 0 | 0 | 0 | 0 | 0 | 0 | 3 | Cocklebur | 1 | 0 | 0 | 0 | 0 | 0 | 4 |
| Crabgrass | 0 | 0 | 3 | 0 | 0 | 0 | 9 | Crabgrass | 1 | 0 | 1 | 0 | 0 | 0 | 4 |
| Downy brome | 1 | 0 | 0 | 0 | 0 | 0 | 0 | Downy brome | 2 | 0 | 1 | 0 | 0 | 0 | 0 |
| Giant foxtail | 0 | 0 | 1 | 0 | 0 | 0 | 5 | Giant foxtail | 1 | 0 | 1 | 0 | 0 | 0 | 2 |
| Morningglory | 2 | 0 | 0 | 0 | 0 | 0 | 8 | Morningglory | 1 | 0 | 1 | 0 | 0 | 0 | 6 |
| Sorghum | 1 | 0 | 0 | 0 | 0 | 0 | 0 | Sorghum | 2 | 0 | 1 | 0 | 0 | 0 | 0 |
| Velvetleaf | 3 | 0 | 4 | 0 | 0 | 0 | 10 | Velvetleaf | 1 | 0 | 8 | 0 | 0 | 0 | 9 |
| Wild oats | 1 | 0 | 0 | 0 | 0 | 0 | 0 | Wild oats | 1 | 0 | 1 | 0 | 0 | 0 | 1 |

What is claimed is:

1. A compound selected from Formula I, N-oxides and agriculturally-suitable salts thereof,

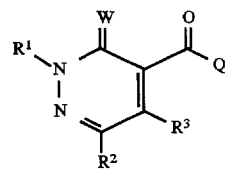

wherein:

Q is phenyl, substituted with $R^4$ and optionally substituted with up to three $R^5$;

provided that, when $R^4$ and an adjacently attached $R^5$ are taken together, then Q is selected from the group

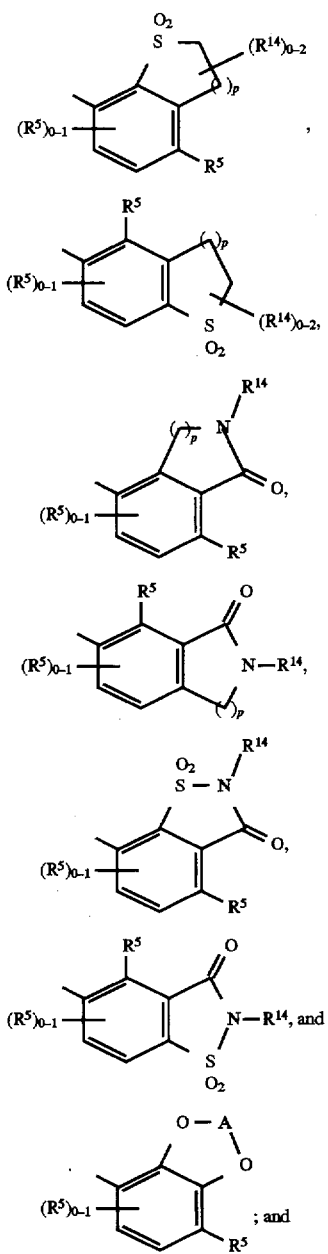

A is —CH₂— or —CH₂—CH₂—, each group optionally substituted with 1-4 halogen;

W is O or S;

$R^1$ is H, $C_1$–$C_6$ alkyl, $C_3$–$C_6$ haloalkyl, $C_3$–$C_6$ alkenyl, $C_3$–$C_6$ haloalkenyl, $C_3$–$C_6$ alkynyl, $C_3$–$C_6$ haloalkynyl, or $C_3$–$C_6$ cycloalkyl;

$R^2$ is H, $C_1$–$C_3$ alkyl, $C_1$–$C_3$ haloalkyl, $C_1$–$C_3$ alkoxy, halogen, or cyano;

$R^3$ is $OR^6$, $C_1$–$C_6$ alkylthio, $C_1$–$C_6$ haloalkylthio, $C_1$–$C_6$ alkylsulfinyl, $C_1$–$C_6$ haloalkylsulfinyl, $C_1$–$C_6$ alkylsulfonyl, $C_1$–$C_6$ haloalkylsulfonyl, mercapto, or halogen;

$R^4$ is $C_1$–$C_4$ alkyl, $C_1$–$C_4$ haloalkyl, $OR^7$, $S(O)_mR^8$, $S(O)_2NR^9R^{10}$, $C(=O)R^8$, $C(=O)OR^8$, $C(=O)NR^9R^{10}$, $NR^{11}R^{12}$, halogen, cyano, or nitro;

each $R^5$ is independently $C_1$–$C_4$ alkyl, $C_1$–$C_4$ haloalkyl, $OR^7$, $S(O)_mR^8$, $S(O)_2NR^9R^{10}$, $C(=O)R^8$, $C(=O)OR^8$, $C(=O)NR^9R^{10}$, $NR^{11}R^{12}$, halogen, cyano, or nitro; or $R^6$ is H, $C_1$–$C_6$ alkyl, $C_1$–$C_6$ haloalkyl, $C_2$–$C_6$ alkoxyalkyl, formyl, $C_2$–$C_6$ alkylcarbonyl, $C_2$–$C_6$ alkoxycarbonyl, $C_2$–$C_6$ alkylamino carbonyl, $C_3$–$C_7$ dialkylaminocarbonyl, $C_1$–$C_6$ alkylsulfonyl, or $C_1$–$C_6$ haloalkylsulfonyl; or $R^6$ is benzoyl or phenylsulfonyl, each optionally substituted with $C_1$–$C_3$ alkyl, halogen, cyano, or nitro;

each $R^7$ is independently $C_1$–$C_4$ alkyl, $C_1$–$C_4$ haloalkyl, $C_3$–$C_5$ cycloalkyl, $C_4$–$C_6$ cycloalkylalkyl, $C_2$–$C_6$ alkoxyalkyl, $C_2$–$C_5$ cyanoalkyl, formyl, $C_2$–$C_5$ alkylcarbonyl, $C_2$–$C_5$ alkoxycarbonyl, $C_1$–$C_4$ alkylsulfonyl, or $C_1$–$C_4$ haloalkylsulfonyl;

each $R^8$ is independently $C_1$–$C_4$ alkyl, $C_1$–$C_4$ haloalkyl, $C_3$–$C_5$ cycloalkyl, $C_4$–$C_6$ cycloalkylalkyl, $C_2$–$C_6$ alkoxyalkyl, or $C_2$–$C_5$ cyanoalkyl;

each $R^9$ is independently H, $C_1$–$C_6$ alkyl, $C_1$–$C_6$ haloalkyl, $C_3$–$C_6$ alkenyl, $C_3$–$C_6$ haloalkenyl, $C_3$–$C_6$ alkynyl, $C_3$–$C_6$ haloalkynyl, or $C_1$–$C_6$ alkoxy; or $R^9$ is phenyl or benzyl, each optionally substituted on the phenyl ring with $C_1$–$C_3$ alkyl, halogen, cyano, or nitro;

each $R^{10}$ is independently H, C–$C_6$ alkyl, $C_1$–$C_6$ haloalkyl, $C_3$–$C_6$ alkenyl, $C_3$–$C_6$ haloalkenyl, $C_3$–$C_6$ alkynyl, or $C_3$–$C_6$ haloalkynyl; or each pair of $R^9$ and $R^{10}$, when attached to the same atom, can independently be taken together as —CH₂CH₂—, —CH₂CH₂CH₂—, —CH₂CH₂CH₂CH₂—, —CH₂CH₂CH₂CH₂CH₂—, or —CH₂CH₂OCH₂CH₂—, each group optionally substituted with 1-2 $C_1$–$C_3$ alkyl;

each $R^{11}$ is independently H, $C_1$–$C_4$ alkyl, $C_1$–$C_4$ haloalkyl, $C_3$–$C_5$ cycloalkyl, $C_4$–$C_6$ cycloalkylalkyl, $C_2$–$C_6$ alkoxyalkyl, $C_2$–$C_5$ cyanoalkyl, formyl, $C_2$–$C_5$ alkylcarbonyl, $C_2$–$C_5$ alkoxycarbonyl, $C_1$–$C_4$ alkylsulfonyl, or $C_1$–$C_4$ haloalkylsulfonyl;

each $R^{12}$ is independently H, $C_1$–$C_6$ alkyl, $C_1$–$C_6$ haloalkyl, $C_3$–$C_6$ alkenyl, $C_3$–$C_6$ haloalkenyl, $C_3$–$C_6$ alkynyl, $C_3$–$C_6$ haloalkynyl, or $C_1$–$C_6$ alkoxy; or $R^{12}$ is phenyl or benzyl, each optionally substituted on the phenyl ring with $C_1$–$C_3$ alkyl, halogen, cyano, or nitro; or each pair of $R^{11}$ and $R^{12}$, when attached to the same atom, can independently be taken together as —CH₂CH₂—, —CH₂CH₂CH₂—, —CH₂CH₂CH₂CH₂—, —CH₂CH₂CH₂CH₂CH₂—, or —CH₂CH₂OCH₂CH₂—, each group optionally substituted with 1-2 $C_1$–$C_3$ alkyl;

$R^{13}$ is H or $C_1$–$C_4$ alkyl;

each $R^{14}$ is independently $C_1$–$C_6$ alkyl, $C_1$–$C_6$ haloalkyl, $C_1$–$C_6$ alkoxy, $C_1$–$C_6$ haloalkoxy, $C_1$–$C_6$ alkylthio, $C_1$–$C_6$ haloalkylthio, hydroxy, or halogen; or two $R^{14}$ bonded to the same carbon atom can be taken together as —OCH₂CH₂O—, —OCH₂CH₂CH₂O—, —SCH₂CH₂S—, or —SCH₂CH₂CH₂S—, each CH₂ optionally substituted with 1-2 CH₃ or 1-2 halogen; or two $R^{14}$ bonded to the same carbon atom can be taken together with the carbon to which they are attached to form C(=O), C(=S) or C(=N—$OR^{15}$); provided that when two $R^{14}$ groups are attached to a carbon atom which is attached to a SO₂ as in Q-1 and Q-2 above then said $R^{14}$ groups are other than taken together as optionally substituted —OCH$_2$CH$_2$O—, —OCH$_2$CH$_2$CH$_2$O—, —SCH$_2$CH$_2$S—, or —SCH$_2$CH$_2$CH$_2$S— and no more than one of said R$^{14}$ groups can be C$_1$–C$_6$ alkoxy, C$_1$–C$_6$ haloalkoxy, C$_1$–C$_6$ alkylthio, C$_1$–C$_6$ haloalkylthio, or hydroxy;

each R$^{15}$ is independently H, C$_1$–C$_6$ alkyl, C$_1$–C$_6$ haloalkyl, C$_3$–C$_6$ alkenyl, or C$_3$–C$_6$ alkynyl;

each m is independently 0, 1, or 2; and each p is independently 1, 2, or 3.

2. The compound of claim 1 which is: 4-[(3,4-dihydro-4,4,5,8-tetramethyl-2H-1-benzothiopyran-6-yl) carbonyl]-5-hydroxy-2-methyl-3(2H)-pyridazinone S,S-dioxide.

3. A herbicidal composition comprising a herbicidally effective amount of a compound of claim 1 and at least one of a surfactant, a solid diluent or a liquid diluent.

4. A method for controlling the growth of undesired vegetation comprising contacting the vegetation or its environment with a herbicidally effective amount of a compound of claim 1.

* * * * *